United States Patent [19]

Kiovsky et al.

[11] 4,410,453

[45] Oct. 18, 1983

[54] ETHYLENE OXIDE CATALYST

[75] Inventors: Joseph R. Kiovsky, Boxborough, Mass.; George W. Young, Brimfield, Ohio; Ramzi Y. Saleh, Baton Rouge, La.

[73] Assignee: Norton Co., Worcester, Mass.

[21] Appl. No.: 344,461

[22] Filed: Feb. 1, 1982

Related U.S. Application Data

[63] Continuation of Ser. No. 181,026, Aug. 25, 1980, abandoned.

[51] Int. Cl.³ .................. B01J 21/04; B01J 21/12; B01J 23/50
[52] U.S. Cl. .................................. 502/253; 549/536; 502/263
[58] Field of Search .......... 252/462, 463, 476, 455 R; 423/628; 549/536

[56] References Cited

U.S. PATENT DOCUMENTS

| | | | |
|---|---|---|---|
| 2,071,119 | 2/1937 | Harger | 252/463 X |
| 2,578,841 | 12/1951 | Robertson et al. | 252/463 X |
| 2,593,100 | 4/1952 | Calingaert | 252/463 |
| 3,823,088 | 7/1974 | Box et al. | 252/463 X |
| 3,962,136 | 6/1976 | Nielsen et al. | 252/454 |
| 4,005,177 | 1/1977 | Weidenbach et al. | 252/463 X |
| 4,061,594 | 12/1977 | Michel et al. | 252/462 |

*Primary Examiner*—W. J. Shine
*Attorney, Agent, or Firm*—Rufus M. Franklin

[57] ABSTRACT

The performance of a silver on alumina catalyst for the oxidation of ethylene to ethylene oxide is improved by the inclusion, in the raw mix for the carrier of an oxide, or oxide precursor, of zinc, lanthanum, or magnesium in the amount of 7 to 40%, calculated as the oxide.

1 Claim, No Drawings

ETHYLENE OXIDE CATALYST

This application is a continuation of application Ser. No. 181,026, filed Aug. 25, 1980.

FIELD OF THE INVENTION

This invention relates to catalysts and catalyst carriers used for the production of ethylene oxide (EO) by the partial oxidation of ethylene (E).

BACKGROUND OF THE INVENTION

The direct oxidation of ethylene to ethylene oxide is unique in that only silver has been found to be an effective heterogeneous catalyst. Under favorable reaction conditions, when the ethylene conversion is low and mass transfer limiting processes are absent, an efficient catalyst can produce a selectivity in excess of 80%. The selectivity is defined to be the ratio of moles of ethylene converted to EO divided by the total ethylene converted; the primary by-product is carbon dioxide.

Commercially, EO is usually formed under conditions of elevated temperature (200°–300° C.) and pressure (150–300 psig). Two major commercial processes exist. The air process is characterized by a low feed concentration of ethylene (<10%) but operates with high ethylene conversions (20–40%); the oxygen process utilizes high ethylene feed concentrations (20–40%) but operates at low ethylene conversions (5–20%). Since, in general, the selectivity decreases with increasing ethylene conversion, the oxygen process shows higher efficiency. The commercial selectivities appear to be in the range of 65–80% depending on operating conditions.

Although the heterogeneous oxidation of E to EO occurs uniquely in the presence of silver, the physical form of the catalyst and presence or absence of impurities have significant effects upon both the activity of the catalyst and the selectivity obtained from the reaction. Silver in the bulk form has been used as an evaporated film, powder, foil, and alloy in various studies. The use of silver in any of these forms has the advantage of promoting high heat transfer rates, enabling rapid removal of the exothermic heat of reaction and thereby helping to prevent over-oxidation. Use of bulk silver, however, is not commercially acceptable because of low specific activity requiring large reactor volumes and large amounts of the expensive metal. Consequently, porous ceramic bodies, known as catalyst carriers, have been used to permit high dispersion of the silver and thereby enable a much more efficient utilization of silver.

The emphasis in carrier selection has been to provide bodies with suitable porosity (40–60%) compatible with mechanical strength and with a low surface area (0.1–1 $M^2/gm$) to insure the absence of strong diffusional resistances for reactants and product gases under reaction conditions. Apart from these physical considerations, the carrier has been required to be inert as far as its catalytic role is concerned. The vast majority of the catalyst patent literature emphasizes the need for an inert carrier. The materials most often used or specified in the catalyst art are alpha-alumina, silica, silicon carbide, and zirconia; although the vast majority of carriers appear to be made from alumina or alumina with small amounts of silica.

The definition of carrier inertness is open to considerable discussion since the presence of low levels of impurities in the carrier may have a beneficial promoter effect on the catalyst performance. In fact, many of the promoters claimed in the catalyst art which are co-deposited with silver on the carrier are already naturally present in the carrier. Typical examples of such promoters are the alkali metals and alkaline earths. Although the role of the promoters is not well defined, it appears that they may act to prevent agglomeration of the finely dispersed silver, cover up surface defects, and inhibit other reaction paths. It is true that in some instances, the majority of these naturally occurring promoters may not be on the accessible carrier surface but may be chemically bound in the bulk of the carrier structure.

A vast catalyst art exists for the deposition of silver on the catalyst carrier. The techniques usually involve either spraying, impregnation, evaporation or precipitation followed by a calcination step in either a reducing or oxidizing environment to activate the silver catalyst. Of these techniques, it appears that impregnation of the carrier with a solution of a suitable silver compound and various promoters is most commonly employed. Typical impregnating solutions may be prepared from aqueous silver nitrate, or more commonly, silver organic complexes of carboxylic acids and organic amines. Such a typical preparation is described by Neilson in U.S. Pat. No. 3,962,136.

As we have just indicated, the prior catalyst art has stressed the need for a non-participatory catalytic role for the carrier and has focused attention on enhancement of catalyst performance by modifying the amount and type of ingredients deposited on the "inert" surface. We believe that the carrier and deposited silver should be considered as a unique catalytic entity with the carrier surface having a strong catalytic influence on the reaction. As a result of this viewpoint, we have discovered that the addition of certain materials to a typical commercial carrier can greatly improve the activity, selectivity or both of the finished catalyst.

SUMMARY OF THE INVENTION

We have discovered that the addition of appropriate amounts of zinc oxide during the manufacture of alpha alumina carriers will result in a carrier which when impregnated with silver will produce a catalyst for the oxidation of E to EO that shows superior activity and selectivity over a conventional catalyst employing a pure alumina carrier. Furthermore, we have found that addition of zinc oxide to a preformed carrier produces an EO catalyst that shows inferior performance to a conventional catalyst.

We have further discovered that the addition of lanthanum oxide during the manufacture of the carrier will result in a catalyst that when compared to a conventional catalyst shows vastly superior activity and also may result in an improvement in selectivity when tested at a comparable ethylene conversion.

We have also discovered that the addition of magnesium oxide during the manufacture of the carrier will result in a catalyst that when compared to a conventional catalyst shows some increase in activity and also may result in an improvement in selectivity when tested at a comparable ethylene conversion.

We have also been able to show that the addition of manganese or titanium oxides during the manufacture of the carrier will result in a catalyst greatly inferior to the conventional catalyst. Furthermore, when preformed conventional carriers are impregnated in such a way as to produce the surface covered with either magnesium oxide or silicon carbide, the resulting catalysts show vastly inferior performance to a conventional catalyst.

DETAILED DESCRIPTION OF THE INVENTION

When a carrier is prepared by mixing various amounts of zinc oxide and alpha alumina and forming a porous body with a surface area of less than about 2 $M^2/gm$, silver can be deposited on that carrier to produce a catalyst superior in activity and selectivity for ethylene oxide production. When either lanthanum or magnesium oxides are used in place of zinc oxides, catalysts can be produced which though they may be inferior to the zinc oxide modified examples, produce catalysts with improved activity when compared to the conventional catalyst.

In the preferred embodiment the level of zinc oxide employed seems to have an important influence and the desirable range appears to be 7 to 40%, or more preferably 10–30%. In addition, the method by which the zinc oxide is incorporated into the carrier body is important. Thus, when zinc oxide is added to a preformed carrier by impregnating the carrier with a suitable solution of zinc nitrate and following this impregnation, the zinc nitrate is oxidized at a low temperature to insure the absence of the zinc-alumina spinel, the resulting body when coated with silver produces a catalyst vastly inferior to the conventional carrier. Only in the cases where zinc oxide and the alumina are subjected to temperatures sufficiently higher to permit some spinel formation, does the presence of some zinc oxide provide a beneficial effect. Furthermore, the stoichiometric amount of zinc oxide for complete spinel formation is not the most beneficial.

The incorporation of lanthanum or magnesium oxide in a similar manner, but in place of the zinc oxide, appears to have somewhat similar, but less beneficial, results. On the other hand, the similar use of titanium dioxide or manganese dioxide, is not desirable; nor is the covering of the preformed alumina surface with silicon carbide, MgO, or zinc oxide.

The preparation of these catalysts and the demonstration of their performance is further described in the following examples.

EXAMPLE 1

As a standard, a conventional carrier useful for the preparation of a silver catalyst for ethylene oxidation was prepared in the usual way known to the art. One hundred parts of calcined alpha alumina was dry mixed with 11 parts of cereal binders, and an organic pore inducing agent, and one part of a processing or forming aid. One to two parts of a clay bond could have been added to enhance mechanical strength of the finished body. Sufficient lubricant such as petroleum jelly and water was added to the mixture to permit the formation of a stiff paste that could be extruded to produce the desirable ring shape of 5/16" diameter. After extrusion, the greenware was permitted to air dry to remove excess moisture before being fired in a gas kiln at the usual temperatures required for alumina bodies, for example U.S. Pat. No. 3,305,492. The resulting carrier had a surface area of less than 0.5 $M^2/gm$ and a porosity greater than 20%.

EXAMPLE 2

A carrier was prepared in the same way as in Example 1 with the exception that five parts of zinc oxide were added to and thoroughly mixed with 95 parts of alumina grain prior to forming into rings and firing.

EXAMPLE 3

A carrier was prepared in the same way as in Example 1 with the exception that ten parts of zinc oxide added to and thoroughly mixed with 90 parts of alumina grain prior to forming into rings and firing.

EXAMPLE 4

A quantity of the carrier prepared as Example 1 was impregnated with an aqueous solution of zinc nitrate of sufficient concentration to permit a pick up of 5% zinc nitrate on the carrier. The impregnated carrier is permitted to air dry before being fired at 1000° F. to convert the zinc nitrate to zinc oxide.

EXAMPLE 5

A quantity of carrier prepared in Example 1 was treated in an identical manner as in Example 4 with the exception that the impregnated solution contained magnesium nitrate and not zinc nitrate.

EXAMPLE 6

A quantity of carrier prepared as Example 1 was impregnated with a solution of polycarbosilane polymer, similar to that described in U.S. Pat. No. 4,052,430, in toluene of sufficient concentration to permit a pick up of 1% silicon carbide. After impregnation and drying the carrier was fired in air at 1200° C. to convert the polymer to silicon carbide.

EXAMPLE 7

Quantities of carriers in Examples 1 through 6 were coated with silver using the typical technique described in the catalyst patent art. In particular, the method employed was that described by Neilson in U.S. Pat. No. 3,962,136 with the exception that no alkaline metal promoters or any other promoters were added. The resulting catalysts all contained 7 to 9% silver as the metal. These catalysts were evaluated for catalytic performance in a recirculating (berty) reactor employing a reactant composition in the reactor of approximately 30% ethylene and 6% oxygen at 200 psig. Helium was the diluent and no chlorine promoters were used. Using a catalyst loading of approximately 100 grams and with a space time of 0.06 kg of catalyst hour/gram mole of ethylene, the activity and selectivity of each catalyst was observed at approximately 200° C. (test 1) and 210° C. (test 2) following an activation period at 220° C. Each test was conducted for 24 hours and the average ethylene conversion and selectivity determined. These values are shown in Table I and two different catalyst prepared from the standard carrier were tested.

EXAMPLE 8

A standard conventional carrier was prepared in a similar manner to that described by Example 1.

EXAMPLE 9

A carrier was prepared in the same way as in Example 8 with the exception that 20 parts of zinc oxide were added to and thoroughly mixed with 80 parts of alumina grain prior to forming into rings and firing.

EXAMPLE 10

A carrier was prepared in the same way as in Example 8 with the exception that 100 parts of zinc oxide were used in place of the alumina grain.

EXAMPLE 11

A carrier was prepared in the same way as in Example 8 with the exception that ten parts of magnesium oxide were added to and thoroughly mixed with 90 parts of alumina grain prior to forming into rings and firing.

EXAMPLE 12

A carrier was prepared in the same way as in Example 8 with the exception that 10 parts of lanthanum oxide were added to and mixed thoroughly with 90 parts of alumina grain prior to forming into rings and firing.

EXAMPLE 13

Quantities of the carriers from Examples 8 and 12 were coated with silver in an identical manner to that described in Example 7. The catalysts were tested as described in Example 7 and the results obtained are given in Table II.

EXAMPLE 14

A standard conventional carrier was prepared in a similar manner to that described in Example 8.

EXAMPLE 15

A carrier was prepared in the same way as in Example 8 with the exception that 20 parts of zinc oxide were added to and thoroughly mixed with 80 parts of alumina grain prior to forming into rings and firing.

EXAMPLE 16

A carrier was prepared in the same way as in Example 8 with the exception that 44.4 parts of zinc oxide were added to and mixed thoroughly with 65.6 parts of the alumina grains prior to forming into rings and firing. This is the stoichiometric amounts of zinc oxide and alumina necessary for complete spinel formation.

EXAMPLE 17

A carrier was prepared in the same way as in Example 8 with the exception that 20 parts of manganese dioxide was added to and mixed thoroughly with 80 parts of alumina grain prior to forming into rings and firing. In order to preserve physical properties similar to the standard carrier firing temperature had to be lowered from the standard by approximately 200° F.

EXAMPLE 18

A carrier was prepared in the same way as in Example 8 with the exception that 20 parts of titanium dioxide were added to and mixed thoroughly with 80 parts of the alumina grain prior to forming into rings and firing.

EXAMPLE 19

A quantity of carrier prepared in Example 14 was impregnated with a solution of a polycarbosilane in tetrahydrofuran of sufficient concentration to provide a 1.3% silicon carbide pick up. The impregnated carrier was permitted to dry at 50° C. before being fired at 1200° C. under a nitrogen atmosphere.

EXAMPLE 20

Quantities of the carriers from Examples 14 through 18 were coated with silver in an identical manner to that described in Example 7. The results obtained are given in Table III.

The specific method of making the carrier, aside from the incorporation into it prior to firing of a source of ZnO, $La_2O_3$ and/or MgO, is not the subject matter of this invention, nor is the particular method of depositing silver on the catalyst. Such methods are known in the art. The following patents teach representative methods of forming the carrier and/or the silver deposit: U.S. Pat. Nos. 2,901,441; 3,172,866; 3,305,492; 3,420,784; 3,526,602; 4,033,903; 4,007,135; 4,102,826; 4,066,575, and U.K. Pat. No. 1,257,352.

While many of the above patents teach the addition of various promoters to the carrier or to the silver, use of the present invention may make such promoters unnecessary, or may enhance their effects, depending upon the particular promoter and the reaction conditions.

TABLE I

CATALYST TEST RESULTS
Examples 1–6

| Example | Modifier | Test 1 Ethylene Conversion, $X_E$ | Test 1 Selectivity, S | Test 2 Ethylene Conversion, $X_E$ | Test 2 Selectivity, S |
|---|---|---|---|---|---|
| 1 | Standard | 3.6 | 70.1 | 6.1 | 63.4 |
| 1 | Standard | 3.8 | 71.6 | 7.1 | 63.1 |
| 2 | 5% ZnO | 3.8 | 68.5 | 6.4 | 61.8 |
| 3 | 10% ZnO | 5.7 | 69.2 | 9.7 | 60.5 |
| 4 | Impregnated $ZnNO_3$ | 3.2 | 60.9 | 6.2 | 49.6 |
| 5 | Impregnated $MgNO_3$ | 2.1 | 46.4 | 3.2 | 40.3 |
| 6 | 1.0 SiC | 2.4 | 57.1 | 4.0 | 51.1 |

TABLE II

CATALYST TEST RESULTS
Examples 8–12

| Example | Modifier | Test 1 Ethylene Conversion, $X_E$ | Test 1 Selectivity, S | Test 2 Ethylene Conversion, $X_E$ | Test 2 Selectivity, S |
|---|---|---|---|---|---|
| 8 | Standard | 3.1 | 69.2 | 6.0 | 60.9 |
| 8 | Standard | 3.1 | 71.9 | 6.4 | 61.0 |
| 9 | 20% ZnO | 5.0 | 73.8 | 9.2 | 65.4 |

TABLE II-continued
CATALYST TEST RESULTS
Examples 8–12

| Example | Modifier | Test 1 Ethylene Conversion, $X_E$ | Test 1 Selectivity, S | Test 2 Ethylene Conversion, $X_E$ | Test 2 Selectivity, S |
| --- | --- | --- | --- | --- | --- |
| 10 | 100% ZnO | 5.6 | 61.6 | 8.5 | 51.6 |
| 11 | 10% MgO | 5.1 | 65.5 | 7.4 | 59.6 |
| 12 | 10% La$_2$O$_3$ | 5.2 | 64.8 | 10.1 | 54.2 |

TABLE III
CATALYST TEST RESULTS
Examples 4–18

| Example | Modifier | Test 1 Ethylene Conversion, $X_E$ | Test 1 Selectivity, S | Test 2 Ethylene Conversion, $X_E$ | Test 2 Selectivity, S |
| --- | --- | --- | --- | --- | --- |
| 14 | Standard | 4.7 | 72.8 | 8.5 | 65.3 |
| 14 | Standard | 4.4 | 73.7 | 7.7 | 67.5 |
| 15 | 20% ZnO | 5.4 | 75.2 | 10.8 | 67.3 |
| 16 | 44.4% ZnO | 3.7 | 73.7 | 8.2 | 64.8 |
| 17 | 20% MnO$_2$ | 1.2 | 60.9 | 2.0 | 52.0 |
| 18 | 20% TiO$_2$ | 1.0 | 75.0 | — | — |
| 19 | 1.3% SiC | 0.0 | — | 0.1 | — |

What is claimed is:

1. A catalyst carrier body supporting metallic silver for the oxidation of ethylene to ethylene oxide, the carrier comprising alpha alumina, optionally including silica, and wherein the improvement consists of the inclusion of from 10 to 30% by weight of ZnO in the carrier body raw mix, and wherein the ZnO is converted to zinc spinel by the raw mix firing.

* * * * *